(12) United States Patent
Hedgecock (10) Patent No.: US 6,830,550 B2
(45) Date of Patent: Dec. 14, 2004

(54) STAIR STEP VOLTAGE ACTUATED MEASUREMENT METHOD AND APPARATUS

(76) Inventor: James Lee Hedgecock, P.O. Box 600, Laguna Beach, CA (US) 92652

( * ) Notice: Subject to any disclaimer, the term of this patent is extended or adjusted under 35 U.S.C. 154(b) by 194 days.

(21) Appl. No.: 10/180,435

(22) Filed: Jun. 25, 2002

(65) Prior Publication Data

US 2003/0236469 A1 Dec. 25, 2003

(51) Int. Cl.[7] ............................................. A61B 5/05
(52) U.S. Cl. ................................................... 600/554
(58) Field of Search .......................... 600/554; 607/66, 607/72

(56) References Cited

U.S. PATENT DOCUMENTS

| | | |
|---|---|---|
| 302,302 A | 7/1884 | Welsh |
| 302,303 A | 7/1884 | Wingate |
| 303,430 A | 8/1884 | Griffin |
| 319,881 A | 6/1885 | Buckley |
| 323,561 A | 8/1885 | Cadwgan |
| 324,106 A | 8/1885 | Hamilton |
| 3,830,226 A | 8/1974 | Staub et al. |
| 4,099,519 A | 7/1978 | Warren |
| 4,305,402 A | 12/1981 | Katims |
| 4,317,457 A | 3/1982 | Guillot |
| 4,387,723 A | 6/1983 | Atlee, III et al. |
| 4,503,863 A | 3/1985 | Katims |
| 4,510,939 A | 4/1985 | Brenman et al. |
| 4,515,168 A | 5/1985 | Chester et al. |
| 4,541,432 A | 9/1985 | Molina-Negro et al. |
| 4,570,640 A | 2/1986 | Barsa |
| 4,582,063 A | 4/1986 | Mickiewicz et al. |
| 4,586,504 A | 5/1986 | de Medinaceli |
| 4,590,949 A | 5/1986 | Pohndorf |
| 4,595,018 A | 6/1986 | Rantala |
| 4,616,660 A | 10/1986 | Johns |
| 4,632,117 A | 12/1986 | James |
| 4,640,286 A | 2/1987 | Thomson |
| 4,646,744 A | 3/1987 | Capel |
| 4,690,145 A | 9/1987 | King-Smith et al. |
| 4,693,254 A | 9/1987 | Mickiewicz et al. |
| 4,723,152 A | 2/1988 | Ohtoli et al. .................. 355/28 |
| D296,470 S | 6/1988 | Leopoldi ...................... D24/23 |
| 4,759,368 A | 7/1988 | Spanton et al. |
| 4,759,377 A | 7/1988 | Dykstra |
| D297,168 S | 8/1988 | Ioffe et al. .................... D24/41 |
| 4,763,656 A | 8/1988 | Nauman |
| 4,765,343 A | 8/1988 | Brenman et al. |
| D299,746 S | 2/1989 | Guldalian, Jr. ................ D24/17 |
| 4,803,986 A | 2/1989 | Dufresne et al. |
| 4,803,988 A | 2/1989 | Thomson |
| 4,940,060 A * | 7/1990 | Gu et al. ..................... 600/554 |
| 5,020,542 A | 6/1991 | Rossmann et al. |
| 5,797,854 A | 8/1998 | Hedgecock |
| 6,029,090 A | 2/2000 | Herbst |
| 6,321,119 B1 * | 11/2001 | Kronberg ..................... 607/66 |

FOREIGN PATENT DOCUMENTS

GB        2 123 698        2/1984

* cited by examiner

*Primary Examiner*—Eric F. Winakur
(74) *Attorney, Agent, or Firm*—Thelen Reid & Priest LLP; David B. Ritchie (57) ABSTRACT

A voltage actuated sensory nerve conduction threshold device uses a stepped square wave voltage for bio-electric stimulation of nerve groups. A step voltage is preset as a percentage of a maximum peak stimulus voltage, which allows current to flow through a patient's skin. As an intensity of the maximum stimulus voltage is varied, the stair step voltage varies as a percentage of the intensity of the stimulus voltage. However, if the stimulus voltage drops to a user set or preset value of stair step voltage, the current flowing through the patient's skin is maintained as the voltage is not allowed to go below that value. This avoids the voltage falling below a cutaneous electrical resistance threshold (CERT) of the patient's skin, at which current conduction ceases.

20 Claims, 11 Drawing Sheets

Nerve Conduction Sensory CPT Examination

Patient Name _____________

Date _____________

| Left | Right | Left | Right | Left | Right |

Lumbar — Left ___ L1 ___ Right ___ ... ___ S2 ___

Cervical — Left ___ C2 ___ Right ___ ... ___ T2 ___

| Left | Right | Left | Right | Left | Right |

STAIR STEP VOLTAGE ACTUATED MEASUREMENT METHOD AND APPARATUS

STATEMENT OF RELATED APPLICATION(S)

The present application is related to European Patent Office Patent Applications EP-01300493.2 entitled "Stair Step Current CPT Measurement Method and Apparatus" filed on Jan. 19, 2001 in the European Patent Office and European Patent Office Patent Application EP-01305831.0 entitled "Stair Step Voltage Actuated Measurement Method and Apparatus" filed on Jun. 22, 2001 in the European Patent Office. Both of these patent applications are in the name of inventor James Lee Hedgecock and are commonly owned herewith.

FIELD OF THE INVENTION

The present invention relates to the field of medical science, and particularly although not exclusively to a method of and apparatus for utilizing bio-electric stimulation.

BACKGROUND OF THE INVENTION

It is known to perform experimental examination for identifying abnormalities in nerve fibers, by applying an electrical stimulation transcutaneously to a patient.

It is well documented that specific current signal frequencies will selectively stimulate distinct types of nerve fibers, for example 5 Hz selectively stimulates type C nerve fibers, 250 Hz stimulates type A-Delta nerve fibers, and 2000 Hz stimulates type A-Beta nerve fibers. This neuroselectivity of frequencies is exploited by a method employed to measure the lowest level of current intensity a subject can recognize with a transcutaneous electrical stimulus. This method is termed current perception threshold (CPT) diagnosis.

A major problem often encountered during CPT testing is that the cutaneous electrical resistance threshold (CERT), the current signal level required before conduction through skin can occur, may be greater than the current perception threshold, the current at which a patient recognizes that a nerve has been stimulated. In subjects with a greater CERT than CPT the intensity of the diagnosis signal is turned up past the actual CPT without the subject recognizing the stimulus, since the current is not flowing through the skin to the nerve fiber. Once the intensity reaches the CERT and the current begins flowing, then the subject may report a false "high" CPT, which is actually the CERT being reached by the applied signal.

Previously, a "constant current" mechanism of bio-electric stimulation was developed in the 1950s and refined in the early 1980s. This later refinement is disclosed in U.S. Pat. No. 4,305,402 (Katim). Katim's constant current mechanism monitored a sine wave current and regulated it so that once the CERT had been reached the current was maintained automatically so as to sustain the signal intensity at sufficient level to allow a continuous flow of current, even though a manually operated intensity control may be turned to zero. Thereby, on the next measurement in a serial test at a same skin site on a patient, the current is not required again to breach the CERT, and the actual CPT can thereby be more accurately measured.

Katim's constant current mechanism works best with a sinusoidal wave form current. However, a sinusoidal current is quite difficult for a patient to recognize within a very narrow range of intensities. Due to the wide fluctuation in measurements obtained using a sinusoidal voltage, measurements must be averaged before meaningful analysis is possible.

A more recognizable stimulus is that of a modulated square wave signal, and in particular, a modulated square wave current. A square wave form current is used in the prior art Medi-DX 7000 CPT diagnostic device of Neuro-DX Associates Incorporated, 445 Dartmoor Street, Laguna Beach, Calif., 92651-1430. This device enables location and quantification of nerve pathology caused by injury, metabolic, and toxic exposures, and provides a screening method for patients prior to invasive examinations and procedures are undertaken. Results of up to 95% accuracy in the detection and quantification of nerve pathology are achievable.

The U.S. Pat. No. 6,029,090 (Herbst) discloses a multi-functional electrical stimulation system having a variety of wave forms including a sine, saw-toothed or square wave form. As with similar prior art stimulation devices Herbst's device provides for a wave form that may be customized in terms of pulse widths and pulse repetition rates. Similarly, GB 2123698 (Biostim) discloses a biological electrical stimulator capable of generating a variety of electrical stimulation wave forms being adjustable with regard to amplitude, pulse rate and burst.

Further teachings of the use of a square wave form being an electrical stimulation signal can be found in U.S. Pat. No. 5,797,854 (Hedgecock), U.S. Pat. No. 4,646,744 (Zion), U.S. Pat. No. 4,690,145 (Minnesota Mining) and U.S. Pat. No. 5,020,542 (Roosmann) however, none of the aforementioned references address the issue of maintaining a flow of current through the skin to the nerve fiber when attempting to measure and determine the CPT in subjects with a greater CERT.

Figure 1:
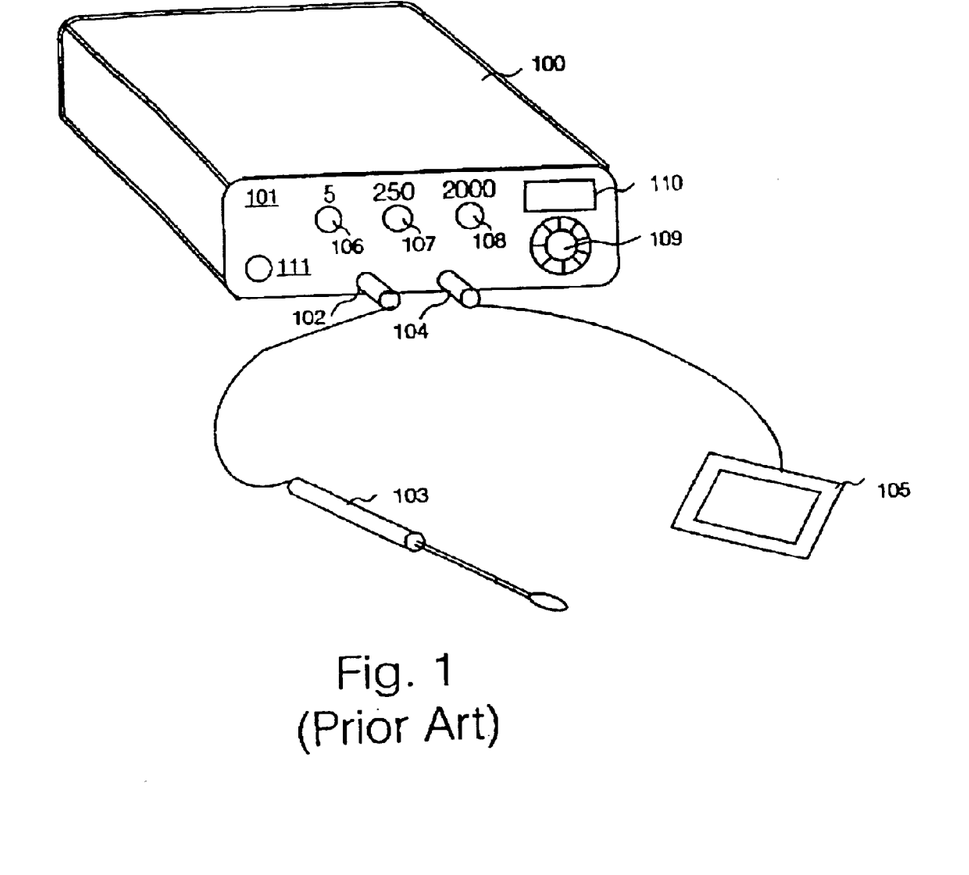
FIG. 1 illustrates schematically the prior art Medi-DX 7000 current perception threshold (CPT) diagnostic device.

Referring to FIG. 1 herein, there is illustrated schematically in perspective view, the known Medi-DX 7000 current perception threshold diagnostic device. The device comprises a casing 100 containing drive electronics for performing current perception threshold measurements on a patient, the casing having a front panel 101 having a first electrical connector port 102 for connection of a probe device 103; a second electrical connector port 104 for a defuse area electrical contact 105; a set of frequency selector switches 106–108 respectively, for selecting test signals having fundamental frequencies corresponding to 5 Hz, 250 Hz and 2 kHz, for testing type C nerves, type A delta nerves, and A-beta nerves respectively; a current intensity control 109 in the form of a rotary dial, having a graduated scale around a circumference of the dial, the rotary dial capable of varying an output current signal in the range 0 to 10 mA between the probe 103 and second electrical contact 105; a liquid crystal display device 110 used to calibrate the current amplitude during manufacture and during after sales service; and an on/off power switch 111.

Figure 2:
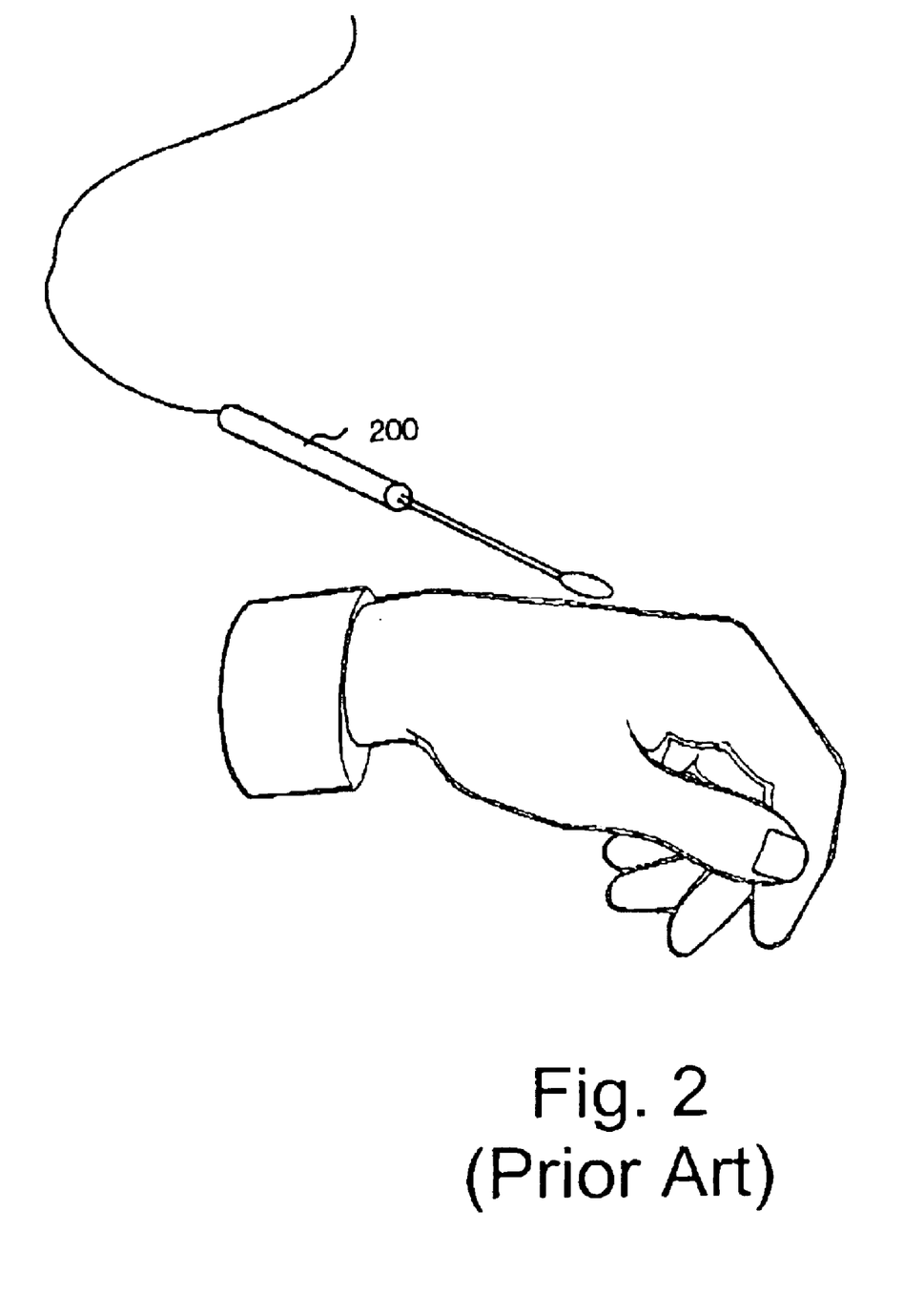
FIG. 2 illustrates schematically placement of a probe contact above a nerve of a patient's left arm.

The usage of the device is known in the art, and is as follows:

A patient is placed into a relaxed position by a medical personnel. The second electrode contact 105 is placed upon a region of the patient's skin to make electrical contact. The second contact 105 is immersed in saline solution, to improve conductivity between the skin and a wide area contact region of the second contact 105. The probe 103, comprises a gold plated tubular contact 200 capable of receiving a cotton bud 203, which is dipped in saline solution to improve conductivity between the gold contact 200 and a patient's skin as illustrated in FIG. 2 herein. The probe 103 and second electrical contact 105 are placed at various positions around the patient's body, and a square wave electrical signal is passed between the probes through the patient's skin, in order to test various nerves around the patient's body as is known in the art.

To test a particular nerve, the medical operator places the probe and contact at specified positions on the persons body and starting from a zero reading, on the rotary current dial 109 corresponding to zero mean current and gradually increases manually the current by rotating the current control 109, until the patient indicates that a sensation is felt. Due to variations in connection resistance between the cotton bud on the end of the probe 103, and the patient's skin, the medical operator repeats this process 3 or more times for every measurement position, in order to reject spurious readings, and to take a set of readings which are consistent with each other, and which can be used to derive an average reading. Since the medical operator relies upon the patient's perception of sensation due to current, the patient may, either voluntarily or involuntarily, give a misleading indication of when a sensation is felt. For example a patient may, by the intonation of the human medical operator's voice, anticipate when to indicate sensation. Therefore the operator must be careful not to give any indication to the patient of when a sensation could be expected.

Figure 3:
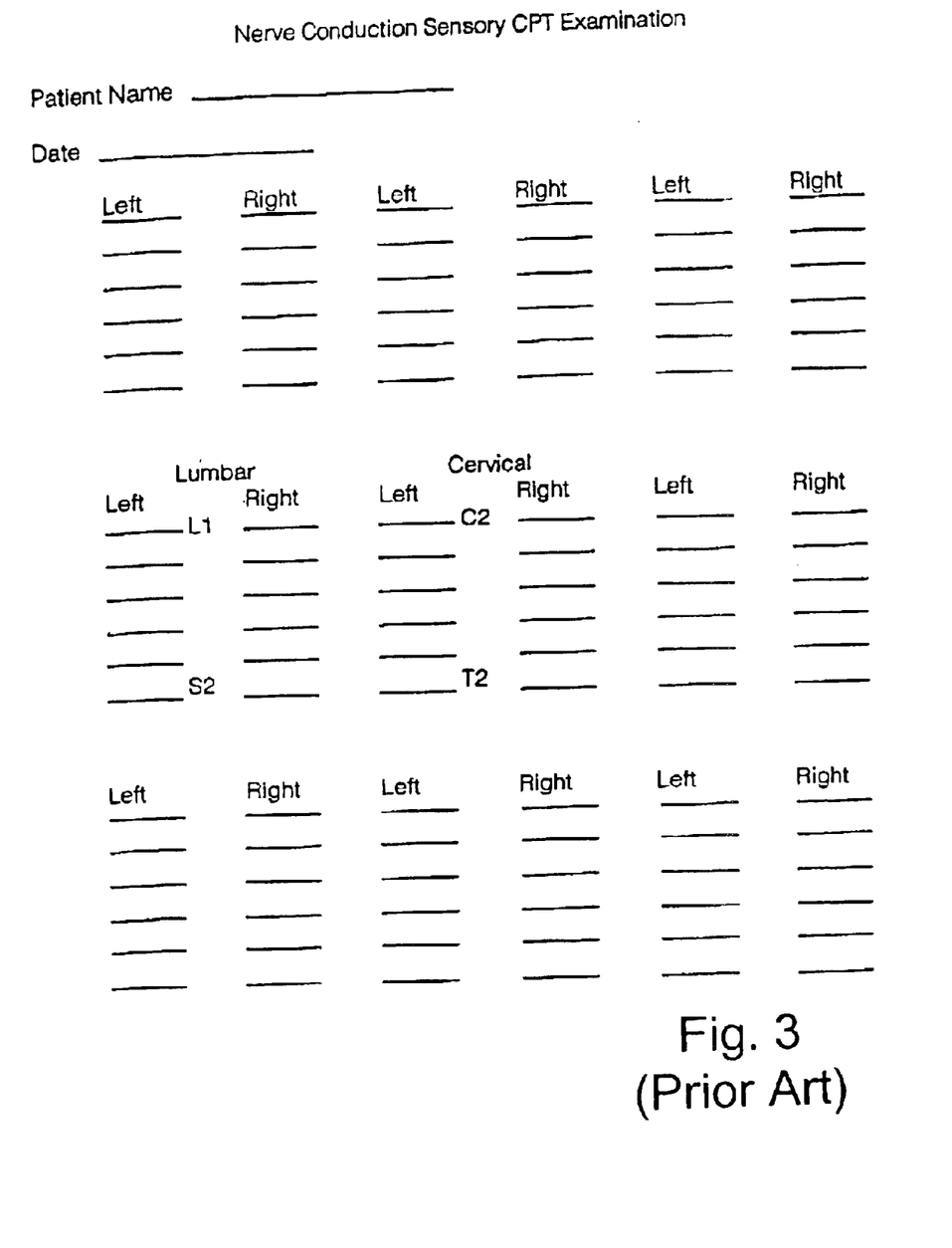
FIG. 3 illustrates schematically one example a record sheet for recording current intensity readings giving rise to responses of nerve stimulation.

For each nerve tested, the operator manually fills in a record sheet similarly as illustrated in FIG. 3 herein. For example for a cervical test, nerves from the C2 to Thoracic 2 nerve may be tested, on both the left side of the patient's body and the right side of the patient's body and entered onto the record sheet as a current intensity reading on a scale 0–100, corresponding to a peak current of 0 to 10 mA. Similarly the medical operator places the probe 103 and second contact 105 on the patient's skin and records readings for the Lumbar L1 to S2 nerves, and other nerve groups as is known in the art.

However, there is a problem in measurement, arising from the electrical conductivity characteristics of a patient's skin. When the probe 103 and second contact 105 are applied to a patient's skin, electrical contact is made via the saline solution, for a current value which has a peak to peak value of a skin conductivity threshold value (CERT), which is determined by the conductive characteristics of the patient's skin. Once the CERT is breached and current is flowing through the skin, provided electrical contact is not lost, and provided the current values does not fall too far below the cutaneous electrical resistance threshold, then current will continue to flow even below the CERT.

However, there is a difficulty in recording readings if the operator returns the rotary current control dial 109 to give a signal too far below the skin's CERT value. Once the current either falls too far below the skin conduction threshold value and current ceases to flow, or if the electrical contact is broken, at a current value below the CERT then the operator must again increase current to exceed the threshold value, before readings can recommence. Additionally, for nerves which respond to currents near the skin conduction threshold value, obtaining accurate readings is made more difficult.

On some patients, the CERT for some skin sites is higher than the current perception level (CPT). In these cases, measurement is difficult because the operator must first breach the CERT, and reduce the current below the CERT, whilst still maintaining current conduction through the skin, in order to test the patients current perception threshold. If at any time the operator reduces the current dial to zero, current conduction will be lost, similarly if the electrical contact between the probe and the skin is broken, then current ceases and measurements must be re-started at the same site. The current value at which current flow stops is characteristic of each individual patient, and is not a known fixed number.

Figure 4:
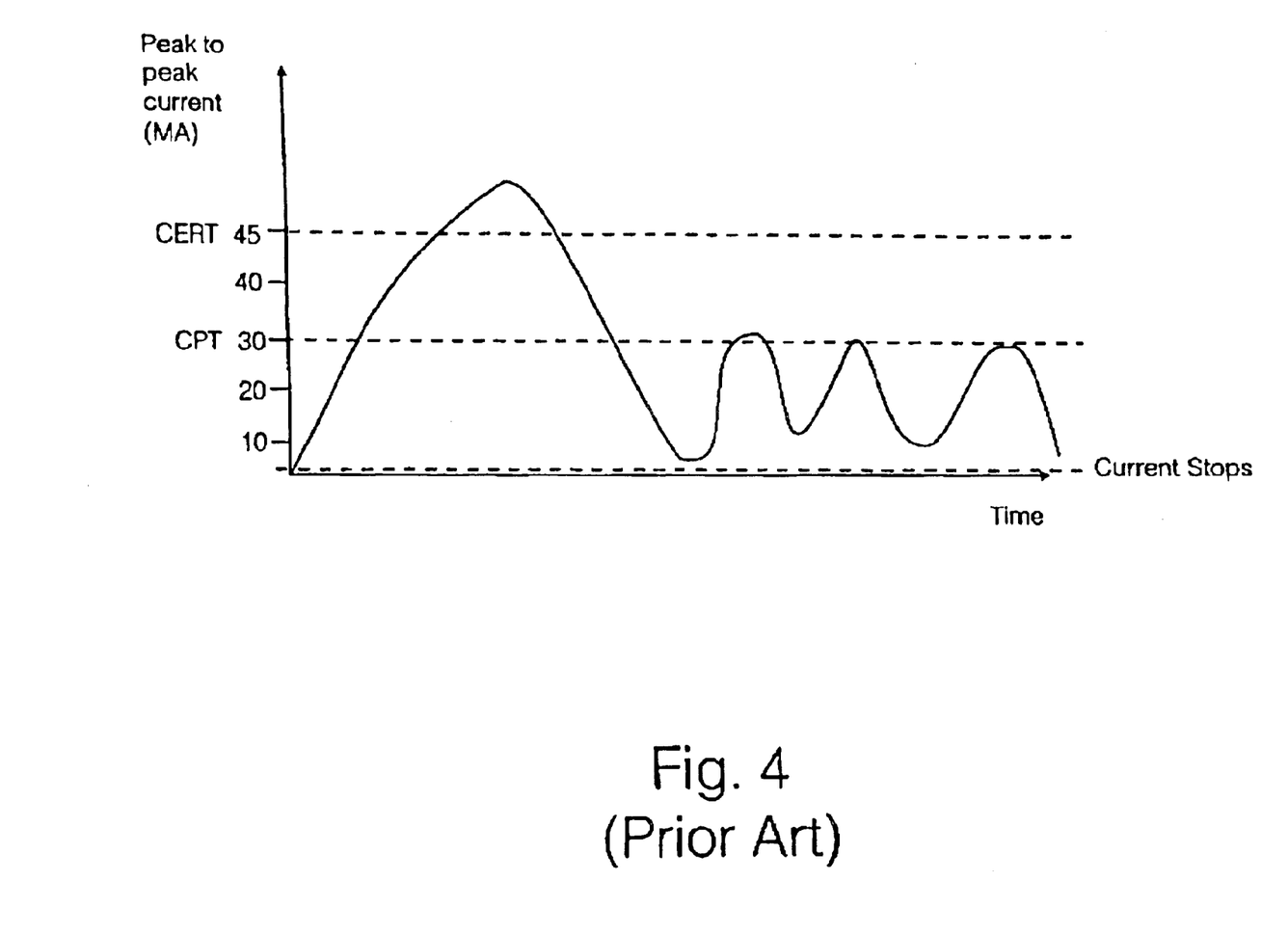
FIG. 4 illustrates schematically a trace of peak to peak current amplitude against time for measurement of a (CPT) level of a patient by a prior art technique.

The problem is exemplified, by the plot of peak to peak current versus time shown in FIG. 4 herein which plots an example of the peak to peak current, as controlled by the medical operator, relative to a skin conduction threshold level 401 and a nerve sensitivity threshold level 402.

In this example, the CERT is above the CPT. Initially, the operator turns the current dial from zero up to, for example a reading of 45, at which point the patient indicates that sensation can be felt. This could either be the CERT, or the CPT. At this stage the operator cannot tell which. The operator therefore reduces the current down to a lower reading of 10, and raises the current again slowly. When the dial reads 30, (the level of the CPT) the patient indicates that a sensation is felt, therefore this is likely to be the CPT. However, to verify that, the operator again drops the current to a value of 10, and slowly raises it through the 30 level, at which the patient again indicates a sensation. To verify this a further time, the operator reduces the current back to 10 and raises slowly through 30 at which point the patient verifies a sensation at the current level of 30. In this case, the CERT has a value of 45, and the measured CPT has a value of 30.

The user protocol to deal with this measurement includes:

At no time can the probe or electrical contact be lifted from the skin sites.

At no time during the sequence of readings can the intensity be turned to zero (and ideally should not be reduced below a reading of 10 corresponding to 1.0 mA).

Once the current is turned down, the patient is asked if they continue to feel a stimulus, and if not, then the current is turned up until they feel the stimulus again.

If an initial higher current measurement is found, then the operator suspects that it is possibly the CERT reading. The operator then turns down the current, but not so far as previously, and asks if the patient continues to feel a stimulus. The operator then turns up the current again until the patient indicates stimulus is felt.

If the same high reading is noted as previously, then that is the actual CPT and it is a true high reading. Otherwise the initial high reading is a breach of the CERT, and the CPT lies below the initial high reading.

As another example, an operator may initially increase the current to a reading of 45 (4.5 mA) turn down the current to 10 and raise it again for a second reading at 45. The current is then turned down to 20 and a third stimulus reading is recorded at a value of 38. Subsequently the current is turned down to 20 again and a fourth reading is measured at a current of 38 and similarly the fourth or fifth reading also a current is measured at 38. In this case, the CPT is at a value of 38 (3.8 mA) and the CERT (the first two readings) is at a value of 45 (4.5 mA).

If the current is allowed to drop below a critical level at which the current stops (typically between 0 and 10) then current conduction through the skin ceases and the measurement sequence must be started again.

Therefore, to obtain a reliable set of readings, the medical operator must not vary the probe contact to the skin between readings, and ideally should not let the current drop to zero during a set of consecutive readings.

The inventor has recognized various problems associated with the utilization of bio-electric stimulation for medical diagnosis based on the variation and monitoring of a current. As the aim of the medical diagnosis applied to a patient is to assess the operation of a nerve and in particular a nerve impulse, and given a nerve impulse is caused by, and is directly correlated with voltage the above diagnosis based on current perception threshold provides an indirect measurement of a nerve impulse. A direct measure of a nerve impulse being provided by the monitoring of voltage intensity.

Figure 5:
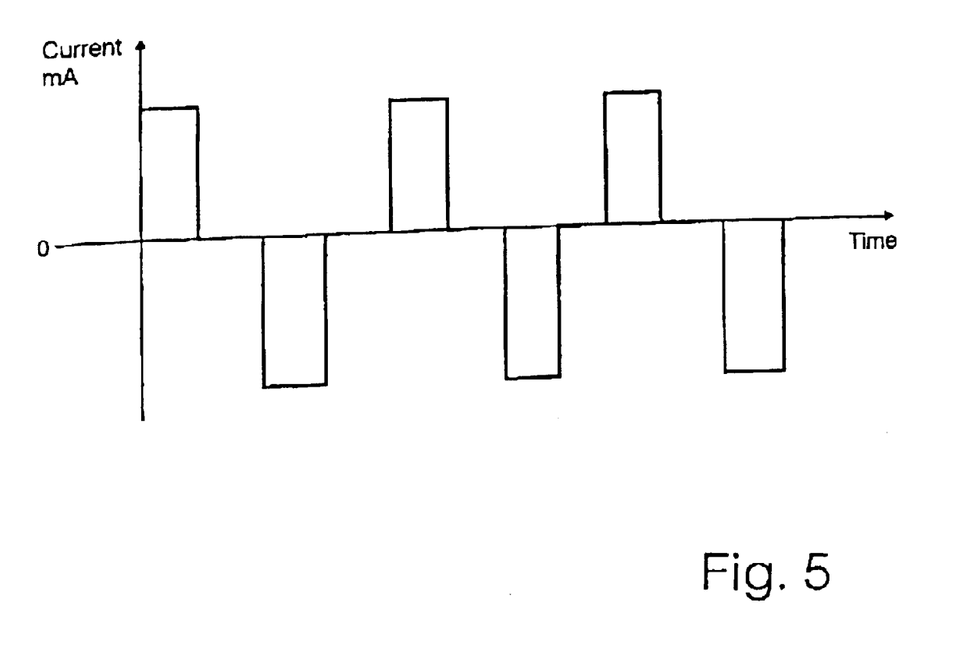
FIG. 5 illustrates schematically a modulated square wave signal, having an alternating current square wave, interrupted by regions of zero current.

The inventor has further realized that a more recognizable stimulus signal than a sine wave or square wave is that of a modulated square wave form as shown in FIG. 5 herein, in which a duty cycle is controlled so as to produce an interval of zero voltage between an alternating positive and negative square wave cycle. However, it has been noticed that this brief interval of zero voltage can interrupt the current flow, especially when testing with lower frequencies. This interruption necessitates breaching the CERT again, with a false high sensory threshold measurement.

BRIEF DESCRIPTION OF THE INVENTION

The bio-electric stimulation method as disclosed in Katim and various of the highlighted prior art, as used to provide an assessment of nerve impulses, assumes, according to Ohm's Law, that the patient's skin has a constant and unchanging electrical resistance. However, this premise is false as, in reality, the skin's resistance is constantly changing and moreover is increasingly varied when current is applied to its surface as in the CPT method, whereby the skin is over-stimulated to release histamine and like substances such that its electrical resistance is substantially altered.

As the method of diagnosis, disclosed herein, involves the measurement of voltage intensity a new terminology is adopted to mirror that of the previously discussed current perception threshold (CPT), this new terminology being Voltage-Actuated Sensory Nerve Conduction Threshold (V-sNCT).

The inventor, through the specific implementations of the present invention, aims to address the above identified problems, namely the inherent inaccuracies involved with a bio-electric stimulation and diagnosis based on current signals and in particular the associated use of bio-electric stimulation using a wave form in the form of a sign or square wave. Based on the fact that the change in a membrane potential, which initiates the nerve impulse, is caused by, and directly correlates with voltage intensity; specific implementations of the present invention aim to provide a method and apparatus utilizing bio-electric stimulation for medical diagnosis based on a direct measurement of the nerve impulse by the measurement of change in membrane potential—measured in volts. The single similarity between the previously discussed CPT diagnosis and the V-sNCT diagnosis according to the specific implementations of the present invention, is that both methods use Neuro-selective frequencies to access the type C fibers (5 Hz), A-Delta (250 Hz) and a A-Beta fibers (2 kHz).

Specific implementations of the present invention further aim to correct the problem of interruption of stimulus signal electric flow by use of a unique electrical wave form which has not been employed previously in experimental bio-electrical stimulation, or in any device used for nerve impulse testing. This new wave form is similar to a modulated square wave form signal with a zero interval, however instead of an interval between square waves being zero, the voltage steps down a controllable percentage of a preceding major part of the wave form. A circuit controls this step voltage as a percentage of a major stimulus voltage. Therefore current flow is maintained since current does not completely stop flowing through the patient's skin. The step voltage is maintained at its highest level until a stair step reset operation returns the step voltage to zero before a new site (nerve) is tested. This mechanism allows any major stimulation wave form to be decreased, but not below a predetermined lower step voltage value.

One object according to the specific implementations of the present invention is to provide a single wave form which maintains current conduction through skin during variation of a stimulus voltage signal amplitude.

A second object of specific implementations of the present invention is to improve the usability of a measurement apparatus using bio-electric stimulation.

According to a first aspect of the present invention there is provided a method of measuring sensitivity of a patient to electrical stimulation comprising the steps of:

attaching a source of electrical signal to a skin region of said patient;

applying an alternating electrical signal from said source, said signal comprising a stimulation signal element for providing electrical stimulation to said patient, and a step signal element for maintaining a flow of said electrical signal through said skin region, said step signal element having an amplitude being set as a percentage of an amplitude of said stimulation signal element; and recording a value of said stimulation signal element at which a nerve stimulation is identified.

Preferably, wherein said electrical stimulation signal is characterized by a wave form having:

a first leading edge raising to a maximum amplitude;

a first trailing edge dropping from said maximum amplitude to a step amplitude, said step amplitude applied for a time duration after said first trailing edge; and a second trailing edge transition reducing said amplitude from said step level, to a zero amplitude.

According to a second aspect of the present invention there is provided an apparatus for applying an electric stimulation signal to a patient, said apparatus comprising:

a signal generator circuit for generating an electrical stimulation signal;

a display device for generating a display of a value of said stimulation signal;

a frequency selector circuit, for selecting a frequency of said electrical stimulation signal; and first and second electrical contacts for making contact of said electrical stimulation signal with a skin region of a patient, characterized in that:

said electrical stimulation signal is alternating, having a positive cycle and a negative cycle, wherein said stimulation signal has a step signal element for maintaining a flow of said electrical signal through said skin region of said patient, said step signal element having an amplitude being set as a percentage of an amplitude of said electrical stimulation signal.

According to a third aspect of the present invention there is provided a method of generating an electrical stimulation voltage for voltage actuated sensory nerve conduction threshold measurements, said method comprising the steps of:

setting a first amplitude level, of a first portion of a cycle of said voltage;

setting a second amplitude level over a second portion of said cycle;

setting said second amplitude level dependent upon said first amplitude level; and setting said second amplitude portion to be maintained at or above a predetermined minimum amplitude value.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

In the drawings.

DETAILED DESCRIPTION

Embodiments of the present invention are described herein in the context of a method and apparatus for carrying out nerve stimulation and conduction measurements. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

In accordance with the present invention, the components, process steps, and/or data structures may be implemented using various types of operating systems, computing platforms, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used without departing from the scope and spirit of the inventive concepts disclosed herein.

Figure 6:
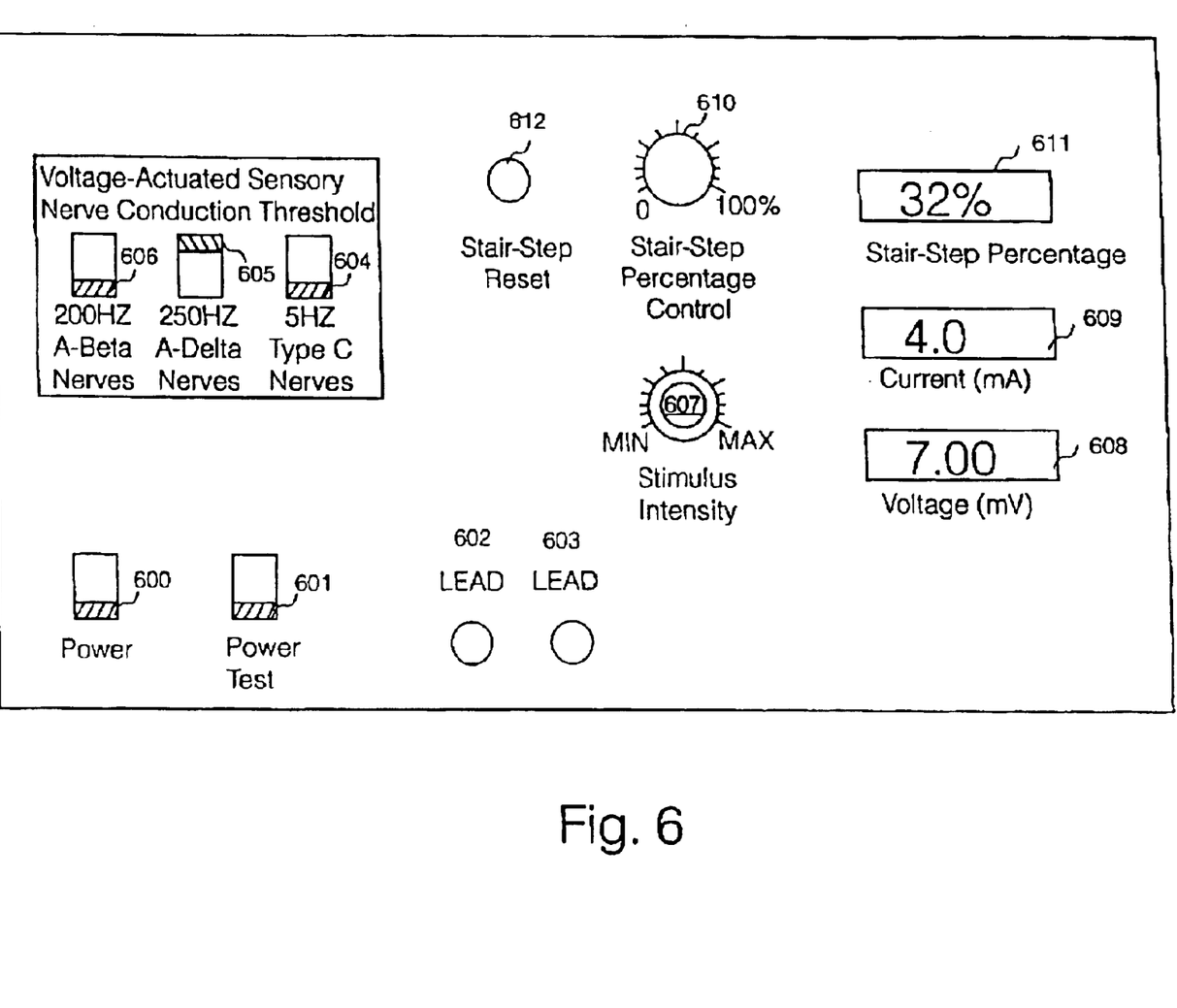
FIG. 6 illustrates schematically a control panel of a novel bio-electric stimulation testing apparatus according to a specific embodiment of the present invention.

Referring to FIG. 6 herein, there is illustrated a schematically a front panel of a bio-electric stimulation test apparatus according to a specific implementation of the present invention. The control panel comprises an on/off power switch 600; a power test switch 601, for testing the power supply to the device; an output port 602 for a probe device, as herein described with reference to FIG. 1; an output lead 603 for a second electric contact device, as described herein above; a first frequency switch 604 set to a 5 Hz frequency for testing type C nerves; a second frequency switch 605 set to a 250 Hz frequency for testing type A-Delta nerves; a third frequency switch set to 2 kHz, set for testing type A-Beta nerves; a voltage intensity control dial 607 having a graduated scale from 0 to 100; a first liquid crystal display 608 for displaying a voltage reading in mV between the probe and the second electrical contact; a second liquid crystal display 609 for displaying a current reading in mA; a second rotary voltage intensity control 610 for controlling a percentage of step voltage, the second rotary control knob, optionally having a graduated scale of 0 to 100%; a third liquid crystal display 611, configured to display a step voltage as a percentage of stimulation voltage; and a step voltage reset button 612, for resetting the step voltage to zero.

Figure 7:
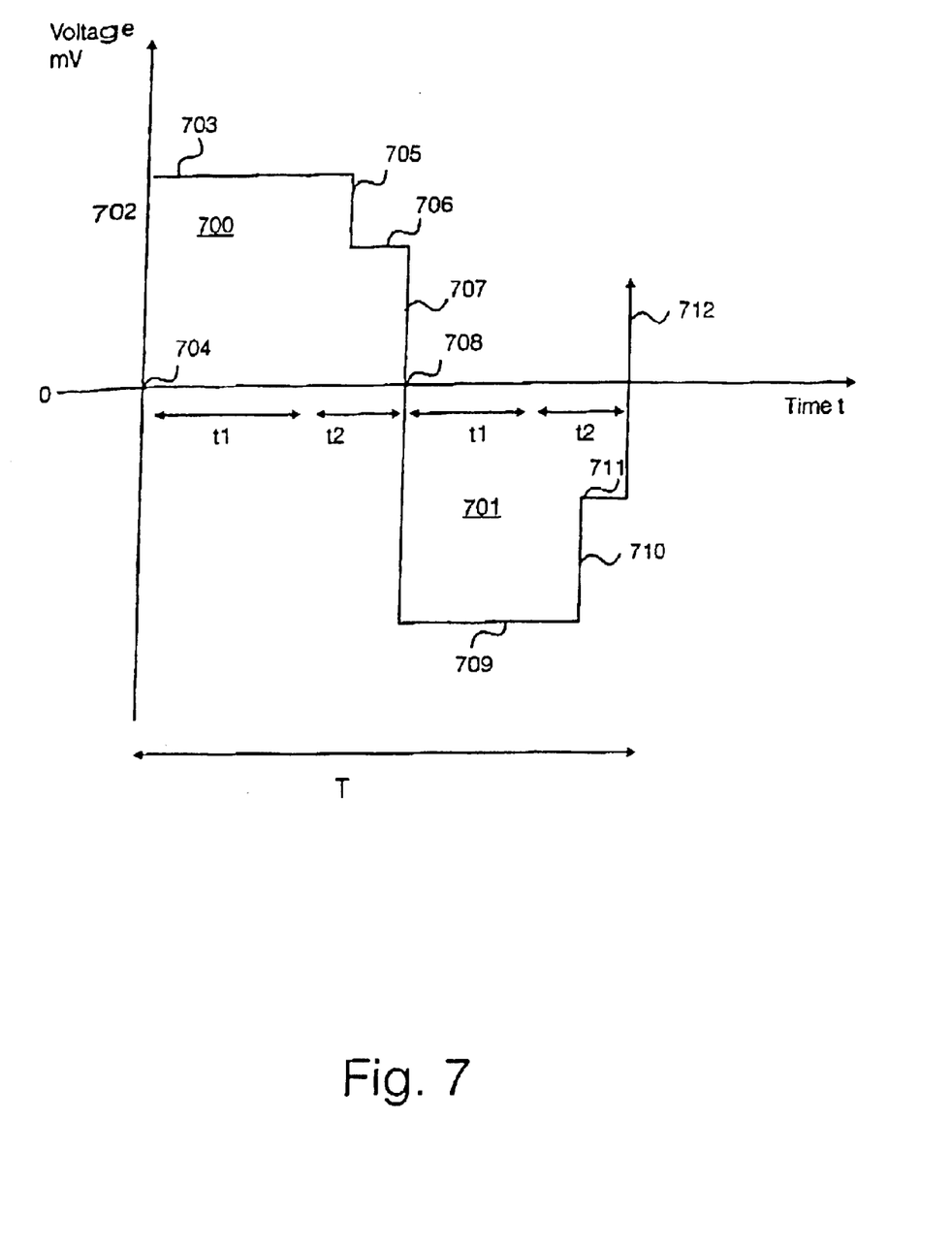
FIG. 7 illustrates schematically an electrical stimulation drive wave form generated by the test apparatus of FIG. 6.

Referring to FIG. 7 herein, there is illustrated a wave form of a drive voltage generated by the stimulation test apparatus between first and second ports 602, 603 for application between a tip of a probe, and a second electrical contact, through a patient's skin. The voltage wave form is characterized by a positive pulse 700 followed by a negative pulse 701, repeating as an alternating voltage. One complete cycle consisting of a positive pulse 700 and a negative pulse 701 has a time duration T. The positive pulse 700 has a positive leading edge 702 followed by a constant stimulation voltage portion 703, followed after a first time period t1 after a positive going zero crossing 704 by a first negative going trailing edge 705, followed by a second constant positive step voltage portion 706 of duration time t2, followed by a second negative going trailing edge 707 crossing through zero voltage at negative going zero point 708, at which the voltage becomes negative; followed by a first negative constant stimulation voltage portion 709 of duration time t1 after the negative going zero crossing 708, followed by a second positive going trailing edge 710, followed by a constant negative step voltage portion 711 of duration t2 after the trailing edge 710 which leads back into a first positive going trailing edge 712 of a next cycle.

The ratio of the time t1 to t2 is variable from $t1/(t1+t2)=0\%$ to $t1/(t1+t2)=100\%$, by adjustment of a potentiometer device or similar.

Figure 8:
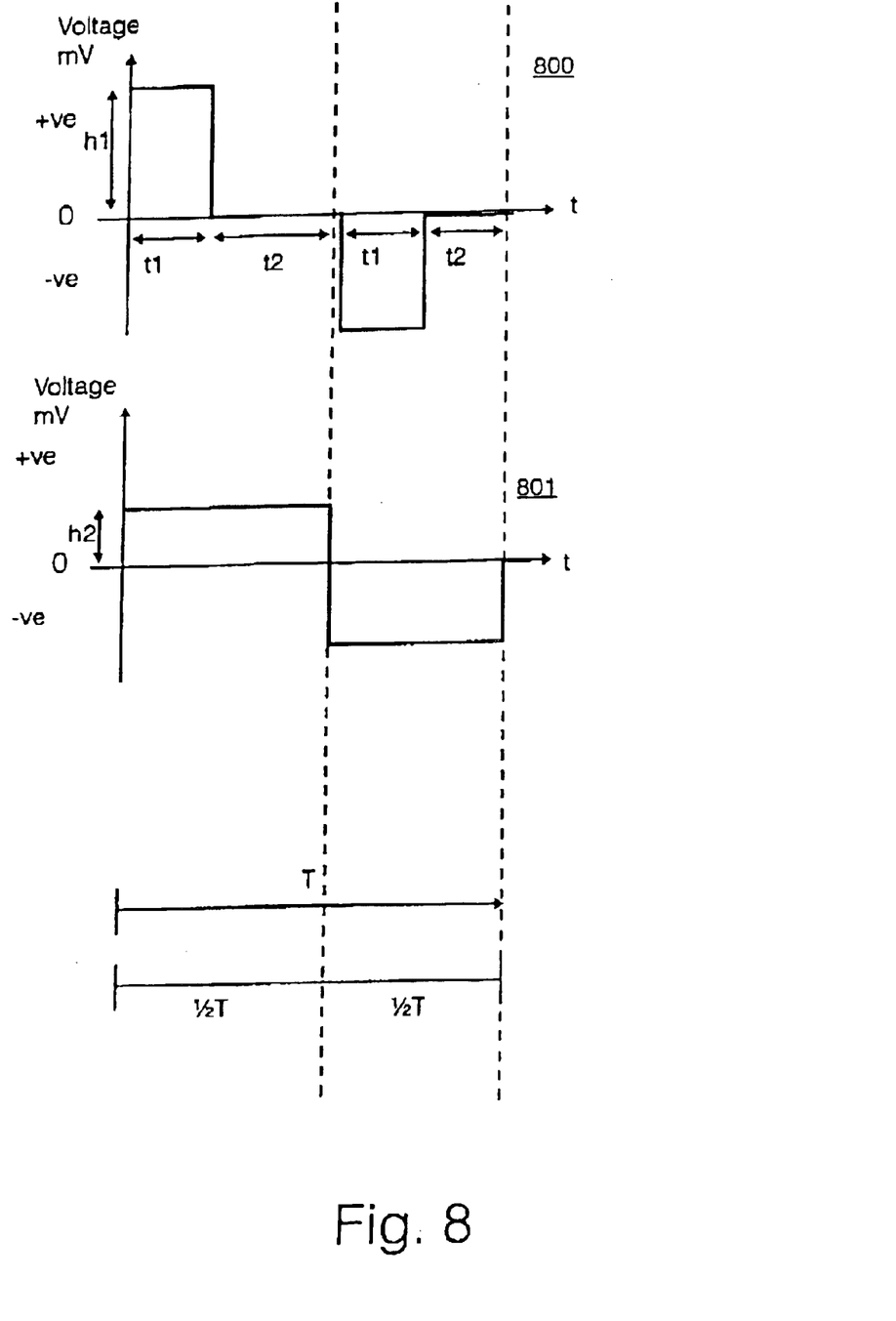
FIG. 8 illustrates schematically component signals of the wave form of FIG. 7.

Referring to FIG. 8 herein, the wave form of FIG. 7 can be constructed from a first pulse wave form 800, and a second pulse wave form 801 by adding these two voltage wave forms. First voltage wave form has a first square wave of voltage amplitude of height h1. The second square wave form 801 has voltage amplitude height h2. The two voltage amplitudes h2 and h1 are independently variable, by variation of stair step percentage control knob 610, so that the ratio h2/(h1+h2) is continuously variable from 0% to 100%, with a human operator selecting the percentage.

A minimum value of h2 can be preset by a suitable mechanism, such as by adjustment of a potentiometer provided for that purpose.

If a first pulse wave form 800 is used alone, then particularly at low frequencies such as 5 Hz, at some sites on some patients, the zero interval between alternating pulses is long enough to stop the flow of current through the patient's skin. Using the modulated pulse wave form 800 alone, without the step level (step amplitude height H2=0% of first square wave amplitude H1), a typical test may be as follows:

Operator raises the stimulus amplitude hi to a first reading of 45, at which the patient indicates stimulus.

Operator turns voltage level down to 10 and takes a second reading raising the voltage to 45, at which the patient indicates stimulus.

Operator turns down the voltage to 20 and raises again to a level of 45, at which the patient indicates stimulus.

Operator turns down the voltage to a level of 30 and raises again to 45 at which the patient indicates stimulus.

Operator turns down the voltage to 40 and raises again to a reading of 45 at which the patient indicates stimulus. The level of 45 could be a CERT, and not the V-sNCT. This could be because the voltage is being interrupted in the period between pulses in the wave form 800, so each time, the CERT must be breached before a patient will indicate sensation.

However, if the step value is applied, at a level of 25% of the stimulus voltage (h2/(h1+h2)=0.25, then the test may run as follows:

Operator increases maximum voltage value to a reading of 45 at which point the patient indicates stimulus.

Operator turns down the voltage level to 10, but because the step level never goes below 25% of 45 (current conduction is maintained throughout the whole of the duty cycle of the wave form).

Operator turns up the voltage through a value of 30, at which point the patient indicates stimulus.

Operator again reduces the dial to 10 (the step voltage maintains the real voltage level), and raises again through level 30 at which point the patient indicates a stimulus.

The cycle is repeated with the operator reducing the dial to 10 again and raising to 30, with the patient indicating a stimulus at level 30.

In this case, the V-sNCT is 30, and the CERT is 45. Because the voltage is not allowed to drop below a predetermined level of the step value set as 25% of 45, current flow is always maintained, so the CERT is not breached for a second time before the initial reading of 45.

If, in the above sequence, the level of 45 is continuously indicated by the patient, then the step down percentage can be increased, to for example 50%. This may indicate that the step level has been set too low by the operator and voltage flow is still being interrupted. However, in the vast majority of cases, a step voltage level of 25% of the peak stimulus voltage gives a valid reading.

Figure 9:
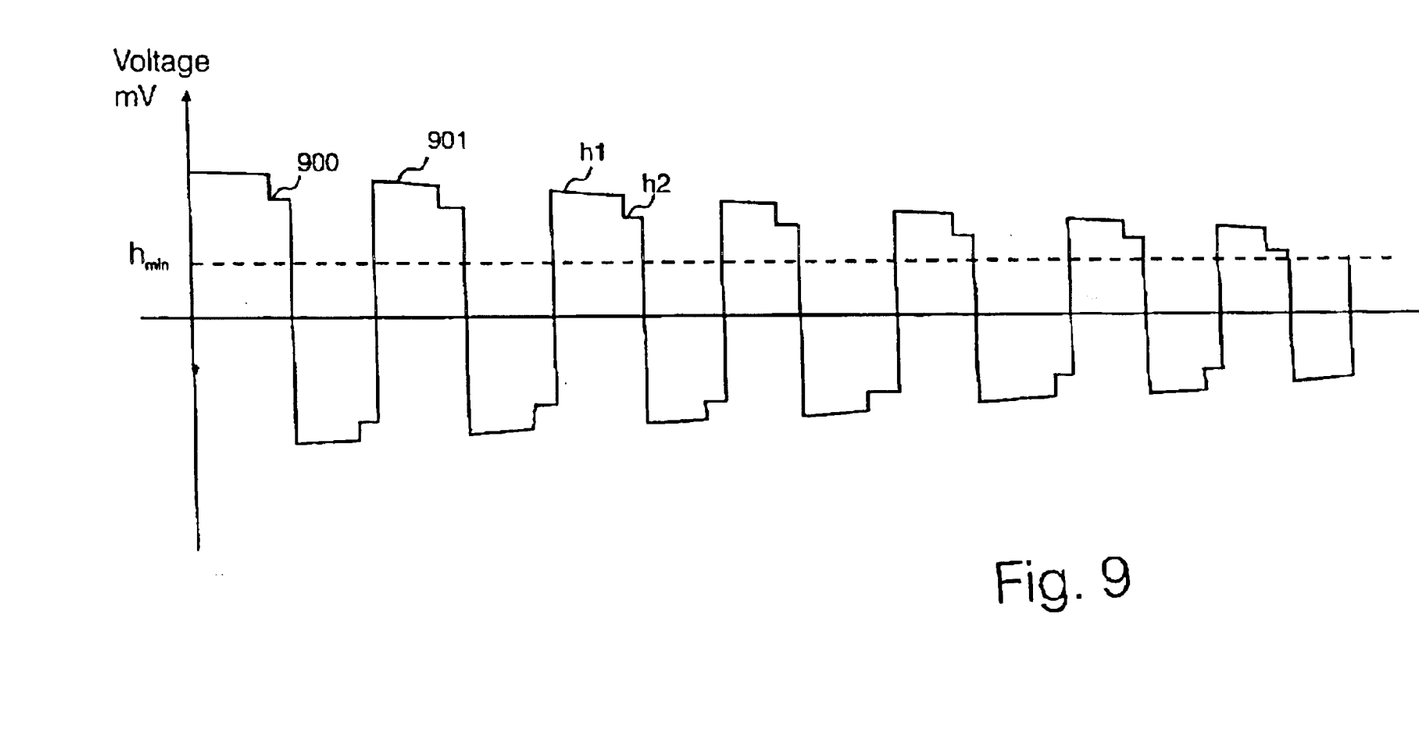
FIG. 9 illustrates schematically an example of an output of the bio-electric stimulation test apparatus of FIG. 6, varying over time.

Referring to FIG. 9 herein there is illustrated schematically an example of the wave form changing over time, as a human operator rotates the stimulus voltage intensity dial 607, reducing the peak stimulus voltage.

Over time, as the peak voltage intensity h1 corresponding to the value of first stimulus voltage value 800 is reduced, because the stair step voltage value h2, corresponding to the step voltage square wave form 801 is locked in as a proportion of the stimulus voltage h1, the step portion of the wave form 800 reduces proportionally with the peak stimulus voltage according to the relationship.

$h2 = h1 \times S$ for all $h2 > h_{min}$ $h2 = h_{min}$ for all h1 less than or equal to $h_{min}$ Where S is user a selectable stair step voltage value as a percentage of stimulus voltage, in the range 0 to 1.0, and $h_{min}$ is a user selectable or factory preset step voltage value with magnitude greater than 0.

Therefore as the voltage is reduced, the maximum stimulus voltage 901 represented by the upper constant portion of the wave form 704 reduces, and whilst the step voltage level 900 is above the preset minimum step value $h_{min}$, the step voltage varies as a proportion of the maximum stimulus voltage. Where the maximum stimulus voltage approaches the preset minimum step voltage $h_{min}$ the peak to peak voltage amplitude of the signal does not fall below $h_{min}$, but is held at the predetermined minimum step voltage value $h_{min}$.

Figure 10:
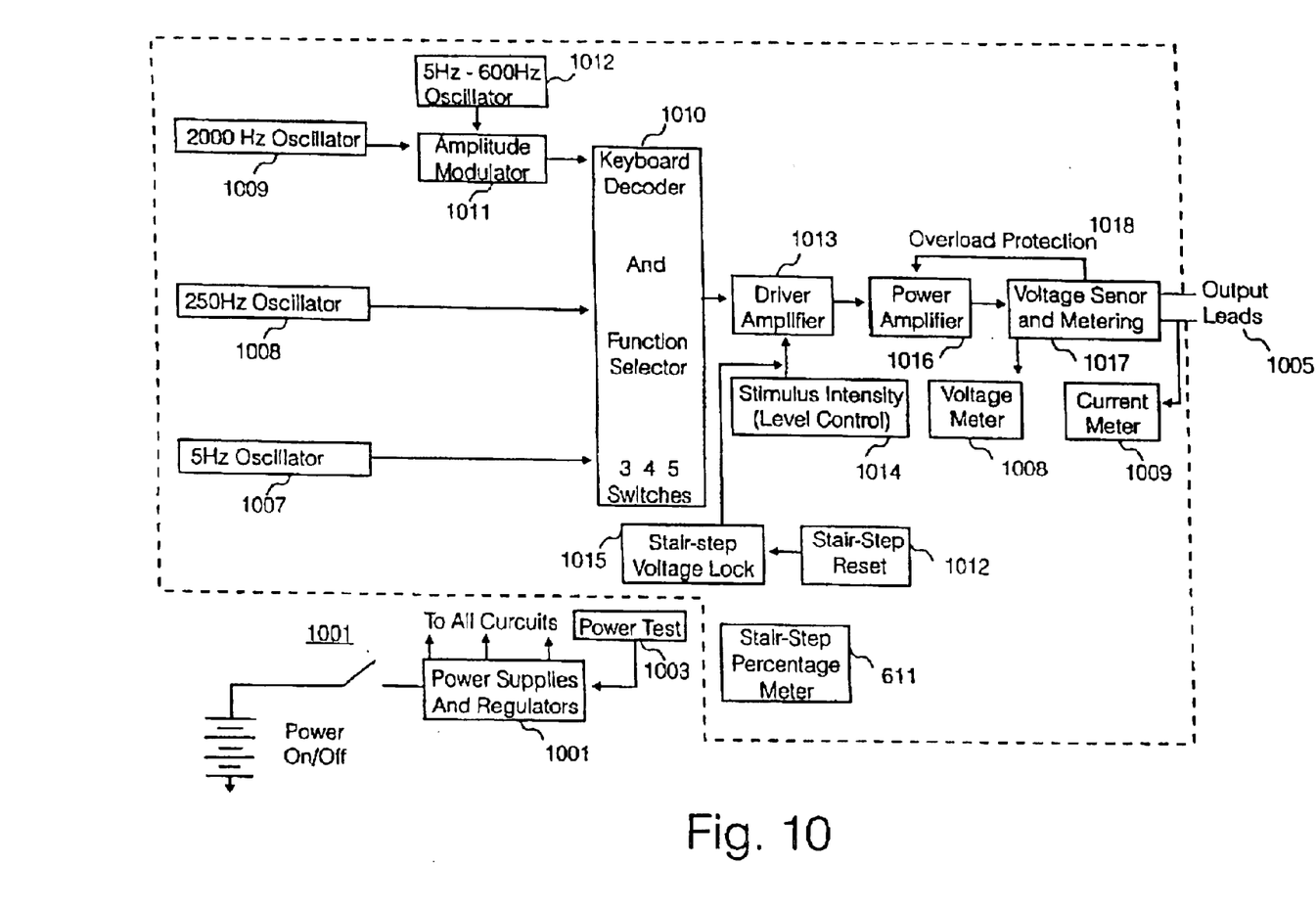
FIG. 10 illustrates schematically a circuit diagram comprising the bio-electric stimulation test apparatus of FIG. 6.

Referring to FIG. 10 herein, there is illustrated schematically a circuit diagram for generating the voltage wave form of FIG. 7. The circuit may be implemented as discrete components, on a circuit board, or as a dedicated chip, for example an application specific integrated circuit (ASIC), comprising analogue and/or digital components, or by a microprocessor, as will be understood by those skilled in the art. The circuit comprises a power supply 1000, being either a battery power supply or a mains voltage derived power supply as is known in the art; a power off/on switch 1001; set of power supplies and regulators providing power to other components; a power test switch 1003 for testing the power supply; and a wave form generation circuit 1004, supplying the wave form to first and second output leads 1005, 1006 respectively corresponding to first and second output ports 602, 603 in FIG. 6.

The wave form generator circuit 1004 comprises a plurality of oscillators 1007–1009 set to oscillation frequencies of 5 Hz, 250 Hz, 2000 Hz respectively; a keyboard decoder and function selector 1010 containing frequency switches 604–606 as described herein before; an amplitude modulator 1011 between the 2000 Hz oscillator 1009 and the keyboard decoder and function selector 1010, the amplitude modulator having an input from a 5 Hz to 600 Hz oscillator 1012; a driver amplifier 1013 receiving an input from the keyboard decoder and function decoder 1010 which selects a wave form type for amplification; a stimulus voltage intensity level control 1014; a stair step voltage lock circuit 1015 for locking the step voltage as a percentage of the stimulation voltage and setting the minimum step voltage $h_{min}$; a stair step reset circuit, activated by stair step reset switch 612; a driver amplifier 1013 being driven by the stair step voltage lock circuit 1015 and stimulus intensity level control 1014; a power amplifier 1016 receiving an output from the driver amplifier 1013 for amplification; and a voltage sensor and metering device 1017 providing a final output to the output leads 1005, 1006 and applying an overload protection by feedback loop 1018, the voltage sensor and metering stage 1017 having the voltage meter 608 and current meter 609 monitoring the voltage and current at the output leads 1005 1006.

Figure 11:
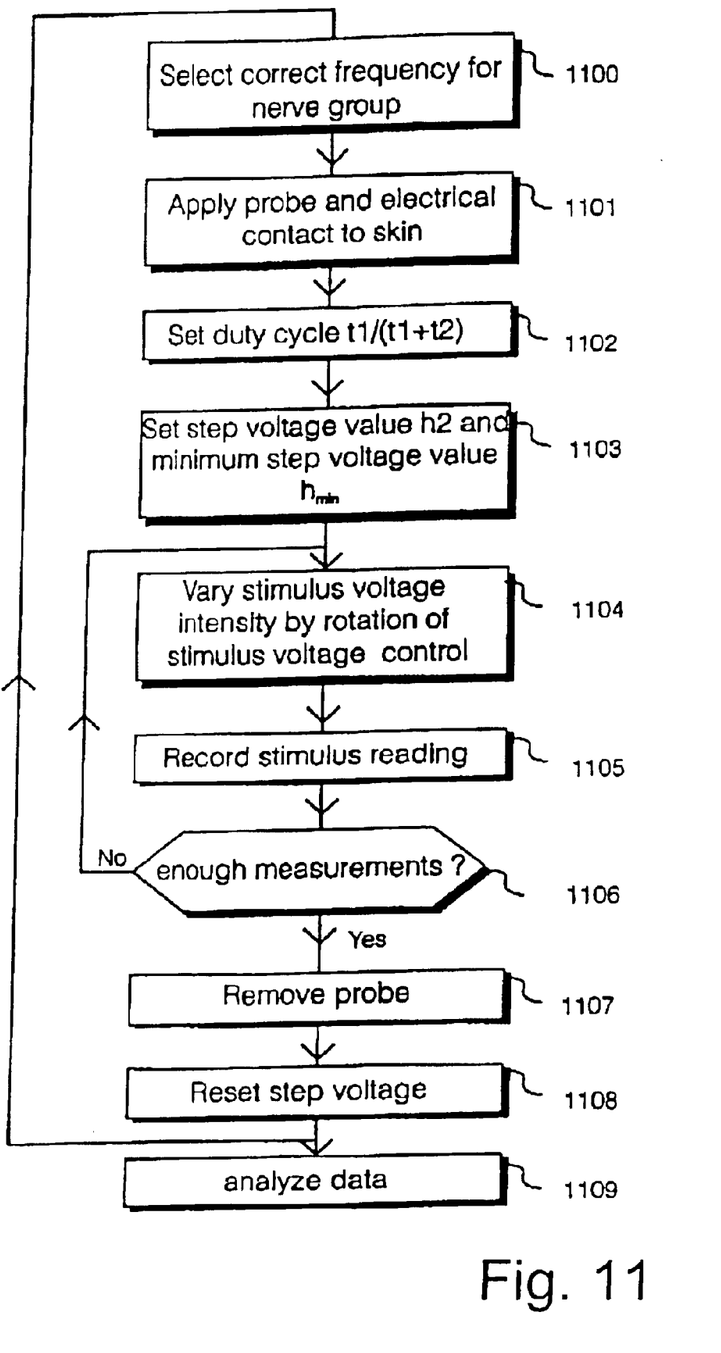
FIG. 11 illustrates schematically steps for usage of the bio-electric stimulation device for recording measurements of nerve sensitivity.

Referring to FIG. 11 herein, there is illustrated schematically a method of use of the stimulation test apparatus. In use, a medical operator applies a probe device and the second electrical contact to a patient's body at the appropriate points, selected for different nerve groups as is known by those skilled in the art. In step 1100, the operator selects a frequency of the signal, either 5 Hz, 250 Hz or 2 kHz in the best mode. In step 1101, the operator applies the probe and electrical contact to the patient's skin. In step 1102, the operator sets the relative time durations of the stimulus voltage and step voltage, within the cycle duration T of the wave form. In the best mode herein favorable results have been found with a ratio t1 as 65% of (t1+t2), in the 250 Hz frequency range, although good performance is found with t2 in the range 25% to 45% of O.S.T. In step 1103, the operator sets the step voltage value for the set of readings to be taken by rotating the stair step percentage control dial 610 and monitoring visually the reading on the stair step percentage display 611. Steps 1100, 1101 and 1102 need not necessarily be performed in the order shown in FIG. 11. For example the duty cycle, once set may be maintained for different readings, and similarly setting of the step voltage value h2 as a proportion of the stimulation voltage value h1. In step 1104 the operator continues to take the first measurement by varying the stimulus voltage intensity by rotation of the stimulus intensity knob 607, and monitoring the stimulus voltage display 608. When the patient indicates that a stimulus is felt on the nerve, then in step 1105 the operator records manually by writing down the stimulus intensity voltagely displayed, onto a record sheet. The steps 1104, 1105 are repeated until in step 1106, enough measurements are recorded for that measurement site. In step 1107, the probe is removed from the patients skin, and in step 1108 the step voltage is reset to zero, ready for the next set of measurements. In step 1109, the data can be analyzed, having been recorded on a record sheet.

In step 1102, the human operator must first find a suitable value of minimum value stair step voltage value $h_{min}$, by raising the stair step voltage to a point where the voltage display 608 displays an actual voltage flowing between the electrodes. Since the voltage is flowing, the human operator knows that the voltage is above the CERT, and can then reduce the value of the minimum value of stair step voltage h2 to a minimum value, where current still flows. Having established that voltage is flowing through the skin, above the CERT, the human operator proceeds to steps 1104, 1105 to rotate the stimulus voltage intensity dial, varying the height h1 and taking the readings as in step 1105.

In step 1104, because the stair step voltage value h2 is automatically varied as the stimulus voltage intensity value hi is varied and cannot go below a preset value $h_{min}$, then the human operator can return the stimulus intensity dial below the CERT, without losing electrical conductivity through the skin, which is maintained by the minimum value $h_{min}$ of the stair step voltage value.

It will be appreciated by those skilled in the art that the invention according to the specific implementation as described herein, may be put into effect by the application and variation of current having a stair step modulated square wave form such that current flow in maintained due to a repeating non-zero stepped current being a percentage of the maximum current peak amplitude.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims.

What is claimed is:

1. A method for measuring sensitivity of a patient to electrical stimulation comprising:
    attaching a source of an electrical signal to a skin region of said patient;
    applying an alternating electrical signal from said source, said signal including a stimulation signal element for providing electrical stimulation to said patient and a step signal element for maintaining a flow of said electrical signal through said skin region, said step signal element having an amplitude being set as a percentage of an amplitude of said stimulation signal element; and
    recording a value of said stimulation signal element at which a nerve stimulation is identified.

2. The method as claimed in claim 1, wherein said amplitude of said step element is set as a fixed percentage of an amplitude of said stimulation signal element.

3. The method as claimed in claim 2, further comprising:
    setting a fixed voltage value of said step signal element amplitude, below which a voltage of said step signal will not be generated.

4. The method as claimed in claim 1, further comprising:
    setting a time duration of said step signal element as a percentage of a total cycle duration of a wave form of said electrical stimulation signal.

5. The method as claimed in claim 4, wherein said percentage is variable in the range of more than 0% to 100%.

6. The method as claimed in claim 1, wherein said alternating electrical signal is characterized by a waveform having:
    a first leading edge rising raising to a maximum amplitude;
    a first trailing edge dropping from said maximum amplitude to said step signal element amplitude, said step signal element amplitude applied for a time duration after said first trailing edge; and
    a second trailing edge transition reducing said amplitude from said step level to a zero amplitude.

7. The method as claimed in claim 1, further comprising:
    varying a time duration of said step signal element relative to said stimulation element, within a cycle of said electrical stimulation signal.

8. The method as claimed in claim 7, wherein a situation of said step signal element is in the range 25% to 45% of a positive or negative cycle of said signal.

9. An apparatus for applying an electric stimulation signal to a patient, said apparatus comprising:
    a signal generator circuit for generating an electrical stimulation signal;
    a display device for generating a display of a value of said stimulation signal;
    a frequency selector circuit, for selecting a frequency of said electrical stimulation signal;
    first and second electrical contacts for making contact of said electrical stimulation signal with a skin region of a patient, characterized in that:
    said electrical stimulation signal is alternating, having a positive cycle and a negative cycle, wherein said stimulation signal has a step signal element for maintaining a flow of said electrical signal through said skin region of said patient, said step signal element having an amplitude being set as a percentage of an amplitude of said electrical stimulation signal; and a recorder recording said value of said stimulation signal at which a nerve stimulation is identified.

10. The apparatus as claimed in claim 9, wherein said apparatus is configured to display a voltage and a current of said electrical stimulation signal and said step signal element.

11. The apparatus as claimed in claim 9, wherein said apparatus is configured to display said amplitude of said step signal element relative to a peak amplitude of said stimulation signal.

12. The apparatus as claimed in claim 9, further comprising a step value percentage control device, capable of controlling a value of said step signal element amplitude relative to a peak amplitude of said stimulation signal.

13. The apparatus as claimed in claim 12, wherein said step percentage control is capable of varying a value of said step element substantially continuously between more than 0% and 100% of said peak amplitude of said stimulation signal.

14. The apparatus as claimed in claim 9, further comprising a step value reset button for resetting said step value after a series of measurements.

15. The apparatus as claimed in claim 9, wherein said generator circuit is capable of setting a minimum voltage value of said electrical stimulation signal.

16. A method for generating an electrical stimulation voltage and performing voltage-actuated sensory nerve conduction threshold measurements, said method comprising:

setting a first amplitude level of a first portion of a cycle of said voltage;

setting a second amplitude level over a second portion of said cycle;

setting said second amplitude level dependent upon said first amplitude level;

setting said second amplitude portion to be maintained at or above a predetermined minimum amplitude value;

applying a nerve stimulation signal with parameters as set to a subject; and recording a value of said first and second amplitude levels at which a nerve stimulation is identified in the subject.

17. The method as claimed in claim 16, wherein said second amplitude level is set to vary as a percentage of said first amplitude level.

18. The method as claimed in claim 16, wherein a first portion of said first amplitude level is variable between more than 0 and 100% of a cycle duration of said voltage.

19. The method as claimed in claim 16, wherein a duration of said second portion is variable between more than 0 and 100% of a duration of said cycle.

20. A method for measuring sensitivity of a patient to electrical stimulation, comprising:

attaching a source of an electrical signal to a skin region of the patient;

applying an electrical signal to the patient, the electrical signal characterized in that it includes a stimulation signal element for providing electrical stimulation to the patient, the stimulation signal element having a first leading edge rising to a maximum amplitude and a first trailing edge dropping from the maximum amplitude to a step signal element for maintaining a flow of the electrical signal through the skin region, the step signal element having a step signal element amplitude being set as a percentage of an amplitude of the stimulation signal element and applied for a time duration after the first trailing edge, and a second trailing edge transition reducing the step signal element amplitude from said step level to a zero amplitude.

* * * * *

UNITED STATES PATENT AND TRADEMARK OFFICE
CERTIFICATE OF CORRECTION

PATENT NO. : 6,830,550 B2
DATED : December 12, 2004
INVENTOR(S) : James Lee Hedgecock It is certified that error appears in the above-identified patent and that said Letters Patent is hereby corrected as shown below:

Column 9,
Line 21, replace "hi" with -- h1 --

Column 11,
Line 54, replace "hi" with -- h1 --

Column 12,
Line 38, after "rising" delete "raising"

Signed and Sealed this

Fifth Day of July, 2005

JON W. DUDAS
*Director of the United States Patent and Trademark Office*